（12） United States Patent
Poher et al.

(10) Patent No.: US 9,019,496 B2
(45) Date of Patent: Apr. 28, 2015

(54) METHOD FOR ESTIMATING THE AMOUNT OF ENTITIES DEPOSITED ON MICROPARTICLES IN SUSPENSION IN A SOLUTION, ASSOCIATED DEVICE AND USE OF SAID DEVICE

(75) Inventors: Vincent Poher, Guines (FR); Frederic Fantoni, Grenoble (FR); Veronique Mourier, Saint Jean de Moirans (FR); Philippe Peltie, Saint Paul de Varces (FR); Frederic Ronzon, Montromant (FR); Christian Valentin, Lyons (FR)

(73) Assignees: Commissariat a l'Energie Atomique et aux Energies Alternatives, Paris (FR); Sanofi Pasteur, Lyons (FR)

( * ) Notice: Subject to any disclaimer, the term of this patent is extended or adjusted under 35 U.S.C. 154(b) by 183 days.

(21) Appl. No.: 13/188,861

(22) Filed: Jul. 22, 2011

(65) Prior Publication Data

US 2012/0044494 A1 Feb. 23, 2012

(30) Foreign Application Priority Data

Jul. 22, 2010 (FR) .................................... 10 03080

(51) Int. Cl.
*G01N 21/00* (2006.01)
*G01N 21/51* (2006.01)
(Continued)

(52) U.S. Cl.
CPC ............. *G01N 21/51* (2013.01); *G01N 21/553* (2013.01); *G01N 21/29* (2013.01); *G01N 15/06* (2013.01)

(58) Field of Classification Search
CPC .......... G01N 33/571; G01N 33/56927; G01N 33/54393; G01N 33/54313; G01N 15/0205; G01N 15/1459; G01N 21/29; G01N 2015/1486; G01N 21/53; C12Q 1/12

USPC .......................................... 356/337, 338, 339
See application file for complete search history.

(56) References Cited

U.S. PATENT DOCUMENTS 4,521,521 A * 6/1985 Abbott et al. ................. 436/517
4,762,413 A 8/1988 Namba et al.
(Continued)

FOREIGN PATENT DOCUMENTS

GB 2 432 660 5/2007

OTHER PUBLICATIONS

French Preliminary Search Report issued Jan. 11, 2011, in French 1003080, filed Jul. 22, 2010 (with English Translation of Categories of Cited Documents).
(Continued)

*Primary Examiner* — Tarifur Chowdhury
*Assistant Examiner* — Isiaka Akanbi
(74) *Attorney, Agent, or Firm* — Oblon, McClelland, Maier & Neustadt, L.L.P.

(57) ABSTRACT

The invention relates to a method for estimating the amount of entities deposited on microparticles in suspension in a solution, and also to an associated device. The method comprises the following steps:
(a) the solution is illuminated with a light source;
(b) an optical signal formed by the scattering, in the solution, of the illuminating light is detected;
(c) the optical signal obtained in step (b) is analyzed in order to obtain an indicator relating to this signal;
(d) the indicator obtained in step (c) is compared with a reference indicator, obtained for a reference solution, the comparison making it possible to estimate the amount of entities deposited on the microparticles.

31 Claims, 10 Drawing Sheets

(51) Int. Cl.
  *G01N 21/552* (2014.01)
  *G01N 21/29* (2006.01)
  *G01N 15/06* (2006.01)

(56) References Cited

U.S. PATENT DOCUMENTS

| | | | |
|---|---|---|---|
| 4,826,319 A | | 5/1989 | Namba et al. |
| 5,100,805 A | * | 3/1992 | Ziege et al. .................... 436/517 |
| 5,858,648 A | * | 1/1999 | Steel et al. ......................... 435/5 |
| 6,674,528 B2 | * | 1/2004 | Adachi et al. ................. 356/336 |
| 7,315,372 B1 | | 1/2008 | Billard et al. |
| 2004/0042008 A1 | * | 3/2004 | Wagner et al. ................. 356/337 |
| 2009/0268202 A1 | * | 10/2009 | Wagner .......................... 356/338 |
| 2009/0325210 A1 | | 12/2009 | Weichselbaum et al. |

OTHER PUBLICATIONS

Y. Piederriere, et al., "Particle aggregation monitoring by speckle size measurement; application to blood platelets aggregation", Optics Express, vol. 12, No. 19, XP002616137, Sep. 20, 2004, pp. 4596-4601.

* cited by examiner

METHOD FOR ESTIMATING THE AMOUNT OF ENTITIES DEPOSITED ON MICROPARTICLES IN SUSPENSION IN A SOLUTION, ASSOCIATED DEVICE AND USE OF SAID DEVICE

The present invention relates to the field of the depositing of entities on microparticles in suspension in a solution.

In particular, the invention relates to a device and a method for estimating the amount of entities deposited on microparticles.

It can in particular be of use in the formulation of vaccines.

This is because the formulation of vaccines involves entities which are antigen molecules, proteins of nanometric sizes, which are deposited by adsorption at the surface of adjuvant microparticles. These adjuvant microparticles are generally particles of aluminum of micron size, in suspension in a solution, for example a saline buffer. This adsorption step is generally carried out in a tank, initially containing the adjuvant microparticles in suspension in a solution, and to which a solution containing antigens is added. There is then a period of stirring, during which the antigens gradually adsorb to the surface of the adjuvant microparticles.

The problem that arises is that of controlling as precisely as possible the amount of antigen adsorbed onto the adjuvant microparticles. This is because this amount is an important parameter that it would ideally be possible to have available during the stirring, by means of a measurement carried out continuously, or at least at regular intervals.

It is known that interactions of antibodies on antigens deposited at the surface of microparticles are capable of changing the optical properties of the solution, and in particular the amount of light scattered according to a given angle.

For example, the document "*Latex immunoagglutination assay for a vasculitis marker in a microfluidic device using static light scattering detection*", Lucas L. J, Biosensors and bioelectronics 22, 2007 (D1) describes how the agglutination of microspheres under the effect of antibody-antigen reactions can be demonstrated by means of an optical method.

More specifically, a solution containing latex microbeads, at the surface of which an antigen has previously been grafted, is placed in a microfluidic network. The addition of antibodies corresponding to this antigen generates agglutination of the microspheres, under the effect of the antigen-antibody reaction. This agglutination is denoted by the term immunoagglutination. This agglutination leads to a variation in light attenuation by the liquid sample according to the concentration of antibodies added to the solution.

According to another example, the document "*Lab-on-a-chip immunoassay for multiple antibodies using microsphere light*", Lucas L. J., biosensors and bioelectronics=23, 2007 (D2) demonstrates a variation in the scattering of light passing through a solution, placed in a microfluidic chip, under the effect of immunoagglutination induced by antigen-antibody reactions taking place at the surface of microspheres.

The surface of the microspheres is initially functionalized with an antigen. When an antibody corresponding to this antigen is added, the antibody-antigen reactions result in agglutination of the microspheres, generating a variation in light scattering in the solution.

The abovementioned methods do not make it possible to measure the amount of antigens deposited at the surface of the microspheres.

Moreover, it has already been proposed to use a Speckle pattern to quantify the light scattering in various solutions. This is, for example, the case of the method presented in the document "*Etude du speckle de milieux diffusants liquides. Application à la détermination de paramètres biophysiques*" [Study of the speckle of scattering liquid media. Application to the determination of biophysical parameters], Y. Piederriere, doctoral thesis presented at the université de Bretagne occidentale [University of Western Brittany] (D3).

Specifically, this document shows how a Speckle pattern can be used to quantify light scattering in various solutions, each solution containing a given concentration of polystyrene microbeads of fixed size, this size ranging, according to solutions, between 0.2 µm and 6 µm.

It is then noted that the analysis of a Speckle image makes it possible to estimate the light scattering coefficient of each solution.

The question of estimating the amount of entities adsorbed at the surface of the microbeads is not, on the other hand, addressed. Moreover, this estimation does not appear to be possible since the analysis of the Speckle image thus carried out does not make it possible to estimate the size of the microbeads contained in each solution. The authors themselves specify that two media consisting of particles of different sizes can produce, for the same attenuation length, Speckle grains of similar sizes, cf. page 93, second paragraph of said document.

It would, however, be advantageous to estimate the amount of entities adsorbed at the surface of microparticles in suspension in a solution.

In the example of vaccine formulation mentioned above, the addition of the solution containing the antigens to the solution containing the adjuvant microparticles is followed by a period of mixing, during which the antigens are gradually adsorbed at the surface of the adjuvant microparticles.

During this period of mixing between the antigens and the microparticles, there is currently no indication of the change in the amount of antigens adsorbed onto the microparticles.

An objective of the invention is, in the context of vaccine formulation, to remedy this problem.

This is because this amount is an important parameter that it would ideally be possible to have available during the period of mixing between the antigens and the microparticles, by means of a measurement carried out in real time.

The term "real time" is intended to mean a period of time compatible with monitoring the process of formulating a vaccine, this period of time typically being less than 10 seconds, and ideally about one second. Ideally, this therefore corresponds to a measurement of the amount of antigens adsorbed onto the adjuvant microparticles at regular intervals, each second.

In addition to verifying vaccine formulation, such a measurement would make it possible to have a better understanding of the mechanisms by which the antigens are adsorbed at the surface of the adjuvant particles, and in particular the adsorption kinetics for these antigens.

The invention is not only directed toward vaccine formulation.

Thus, and more generally, another objective of the invention is to estimate the amount of entities adsorbed onto microparticles in suspension in a solution.

An objective of the invention is also to precisely estimate the amount of entities adsorbed onto microparticles in suspension in a solution.

Even more generally, an objective of the invention is to estimate the amount of entities deposited on microparticles in suspension in a solution.

In order to achieve at least one of these objectives, the invention proposes a method for estimating the amount of entities deposited on microparticles in suspension in a solution, comprising the following steps:

(a) the solution is illuminated with a light source;
(b) an optical signal formed by the scattering, in the solution, of the illuminating light is detected;
(c) the optical signal obtained in step (b) is analyzed in order to obtain an indicator relating to this signal;
(d) the indicator obtained in step (c) is compared with a reference indicator, obtained for a reference solution, the comparison making it possible to estimate the amount of entities deposited on the microparticles.

The method according to the invention may comprise the following characteristics, taken alone or in combination:
the indicator obtained in step (c) corresponds to the light intensity of the optical signal;
the optical signal detected in step (b) is at least one speckle image;
the indicator obtained in step (c) corresponds to an average size of the speckles of said at least one speckle image;
the indicator obtained in step (c) corresponds to the average intensity of said at least one speckle image;
the entities have a size of between 1 nm and 10 μm and the microparticles have a size of between 0.1 μm and 100 μm;
the microparticles are aluminum microparticles;
the solution is chosen from one of the following solutions: aqueous solution, for example a saline aqueous solution, or trishydroxymethylaminomethane solution;
the solution forms a turbid solution of microparticles in suspension;
step (a) is carried out with a coherent light,
step (a) is carried out with a monochromatic light;
the reference solution involved in step (d) is a solution identical to the solution illuminated in step (a), with the exception of the presence of entities.

In order to achieve at least one of these objectives, the invention also proposes a device for estimating the amount of entities deposited on microparticles in suspension in a solution, comprising:
a light source intended to illuminate the solution;
an imager for detecting an optical signal formed by the scattering of the light in the solution; and
a means for analyzing and processing the optical signal thus detected, in order to obtain an indicator that can be compared with a reference indicator obtained for a reference solution, the comparison making it possible to estimate the amount of entities deposited on the microparticles.

The device according to the invention may comprise at least one of the following characteristics, taken alone or in combination:
the light source and the imager are integrated in a sealed receptacle that can be immersed in the solution;
the analyzing and processing means is integrated in said sealed receptacle;
it also comprises a container intended to contain the solution;
the light source and the imager are placed on either side of the container;
it comprises a means, placed before the imager, for eliminating the light photons that have scattered several times in the solution;
the means for eliminating the light photons that have scattered several times in the solution is a diaphragm;
the light source is a source of coherent light, for example formed by a laser;
the imager is a matrix imager, for example of CCD or CMOS matrix or photodiode matrix type;
the matrix imager detects a speckle image as an optical signal;
the imager is formed by a photodiode.

The device according to the invention may more particularly be used for estimating the amount of entities adsorbed and/or desorbed on the microparticles in suspension in the solution.

Other characteristics, aims and advantages of the invention will be stated in the detailed description hereinafter, given with reference to the following figures:

FIG. 1 sets out the principle of the method according to a "transmission" configuration;

Figure 4:
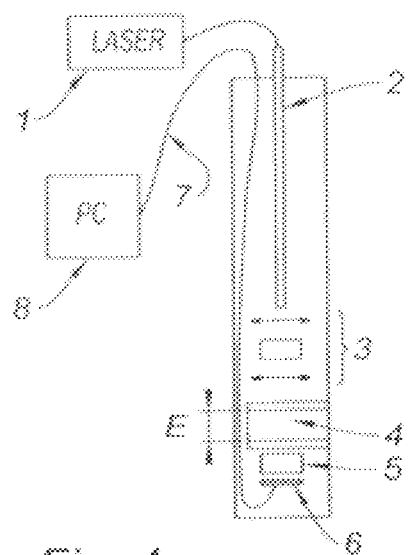
FIG. 4 represents the device used for the tests carried out in order to show the feasibility of the method according to the invention.
Figure 23:
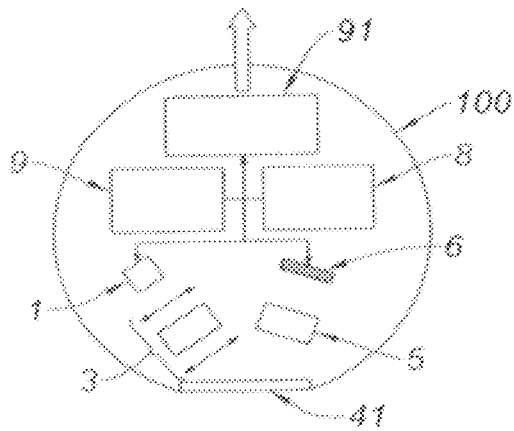
Figure 5:
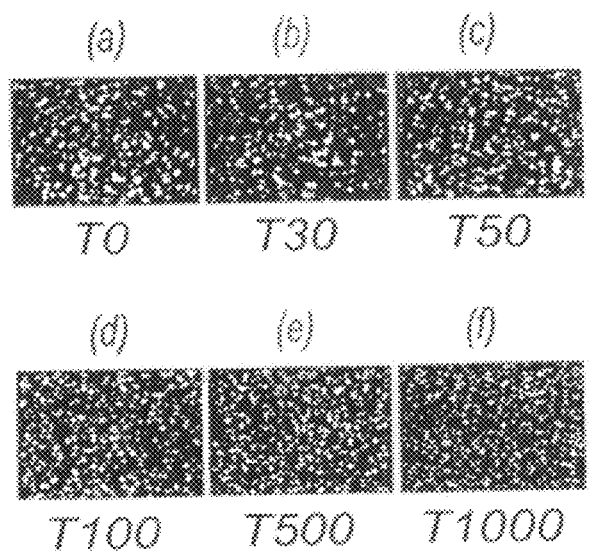
Figure 6:
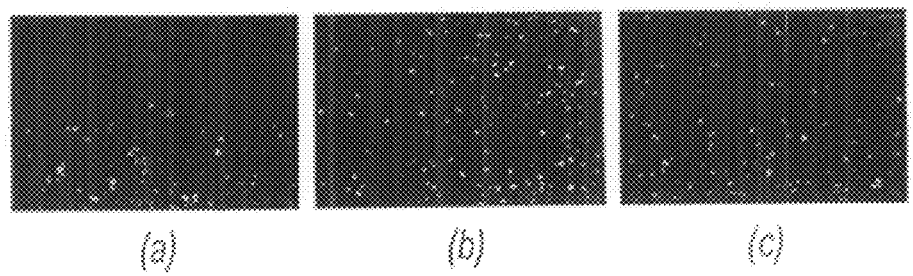
Figure 7:
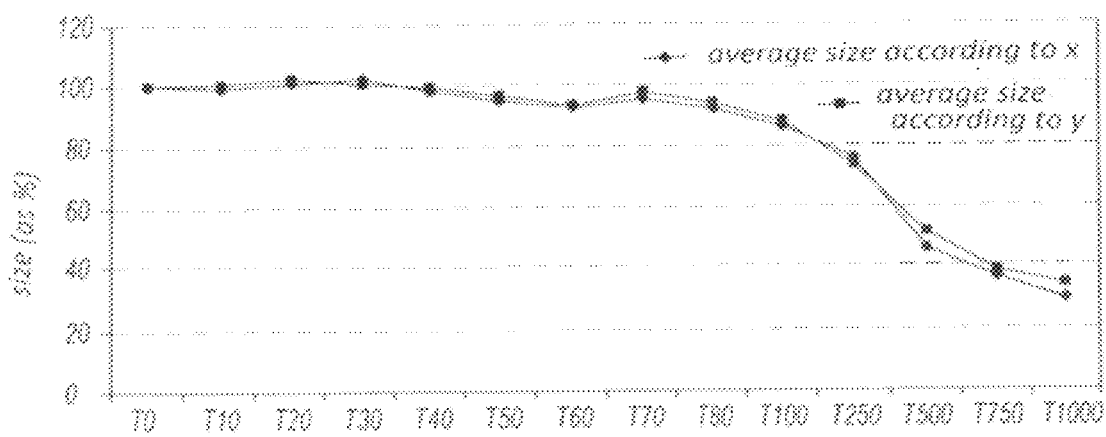
Figure 22:
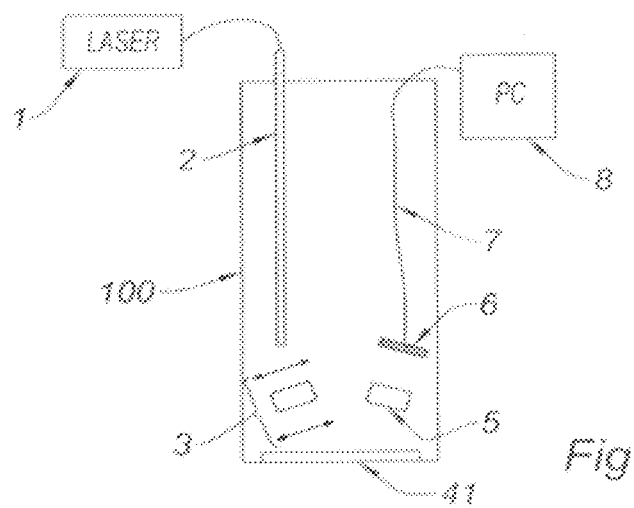
Figure 8:
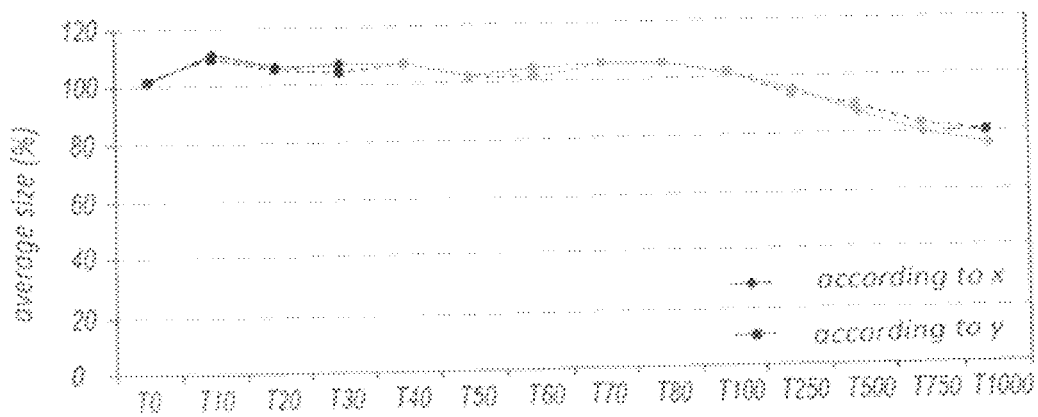
Figure 9:
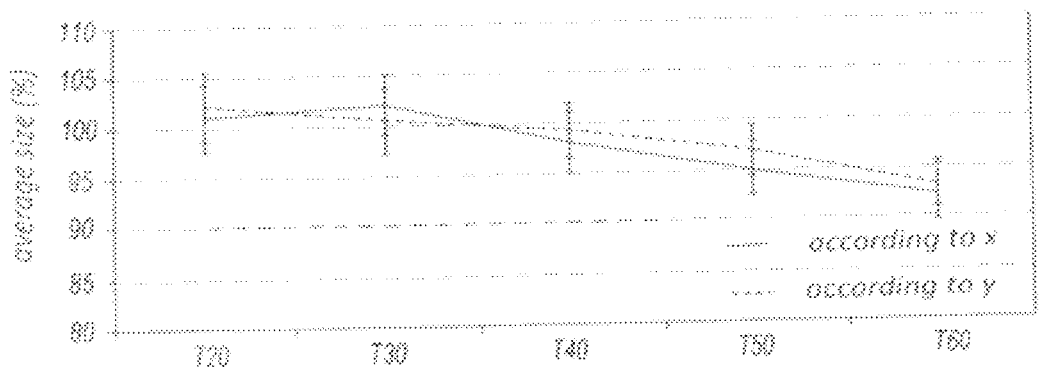
Figure 10:
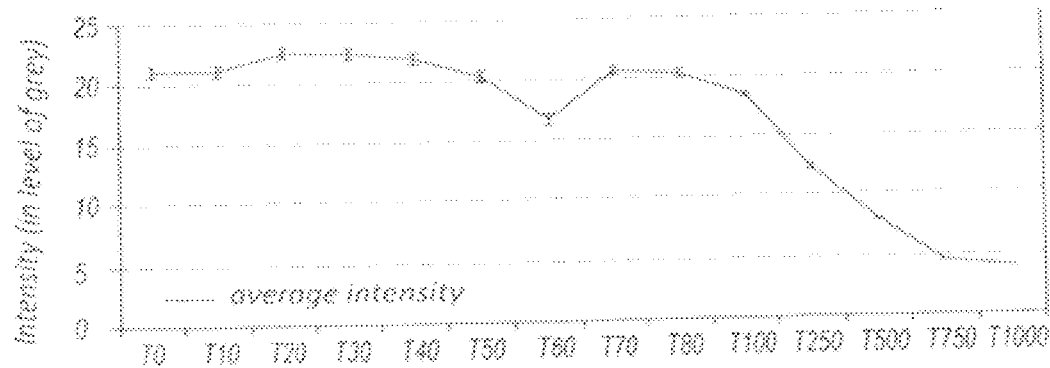
Figure 11:
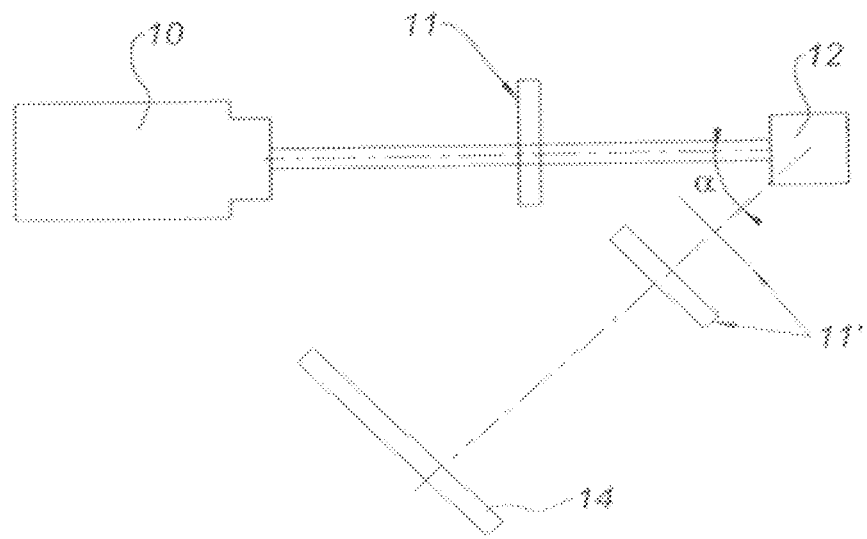
Figure 12:
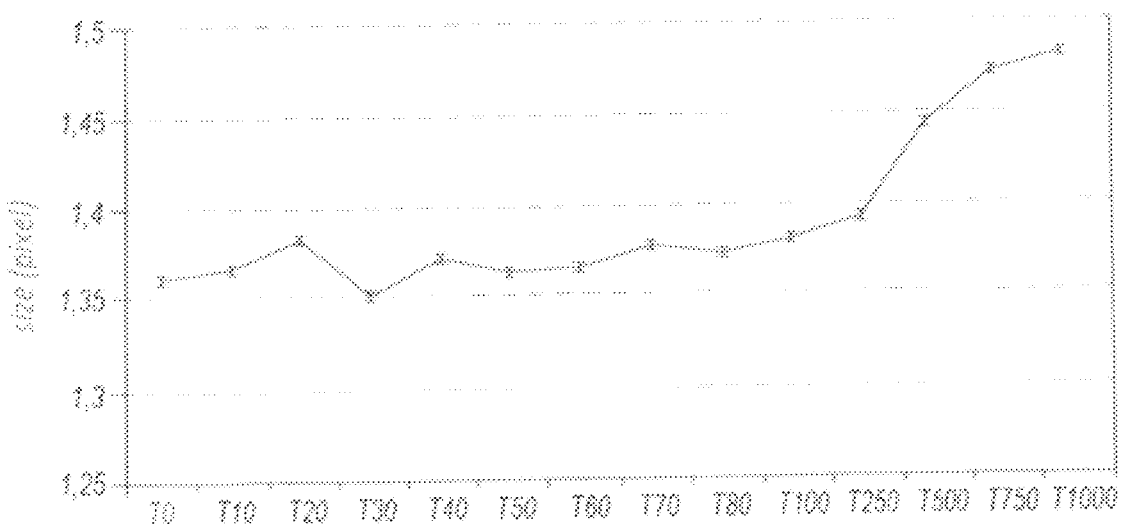
Figure 13:
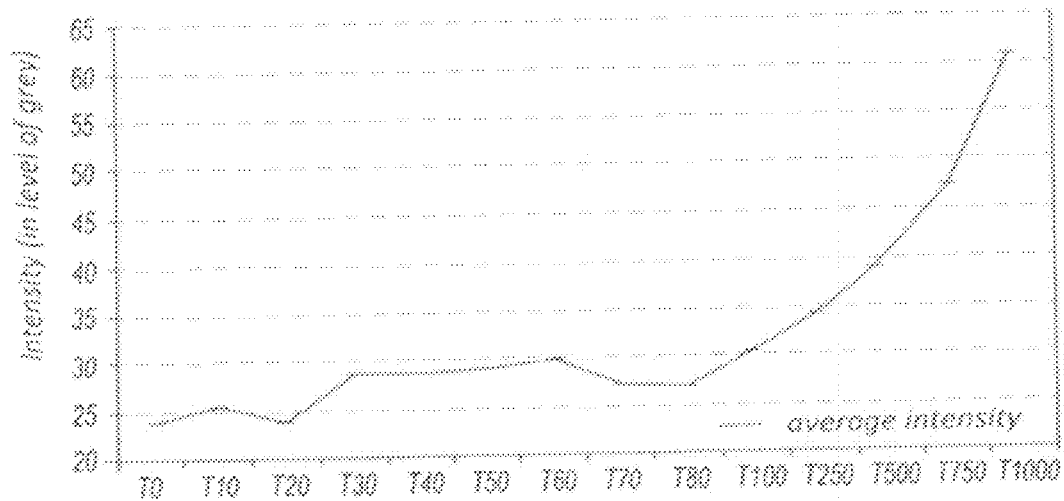
Figure 14:
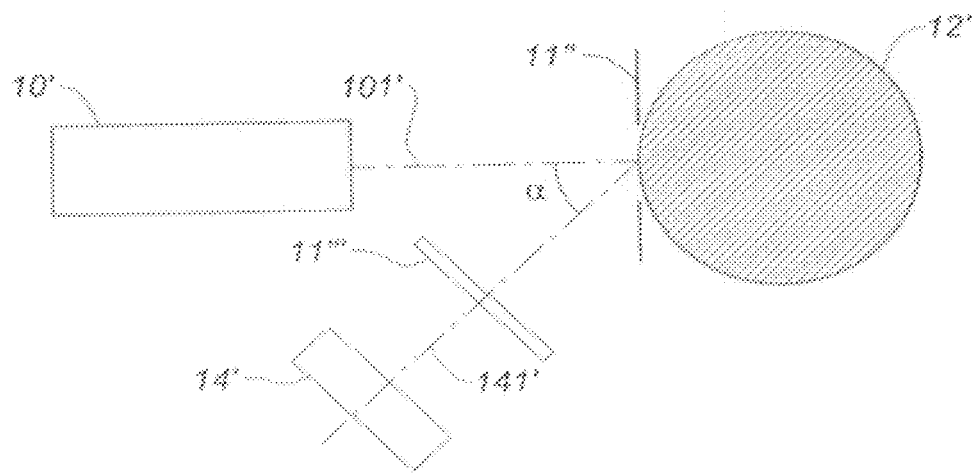
Figure 15:
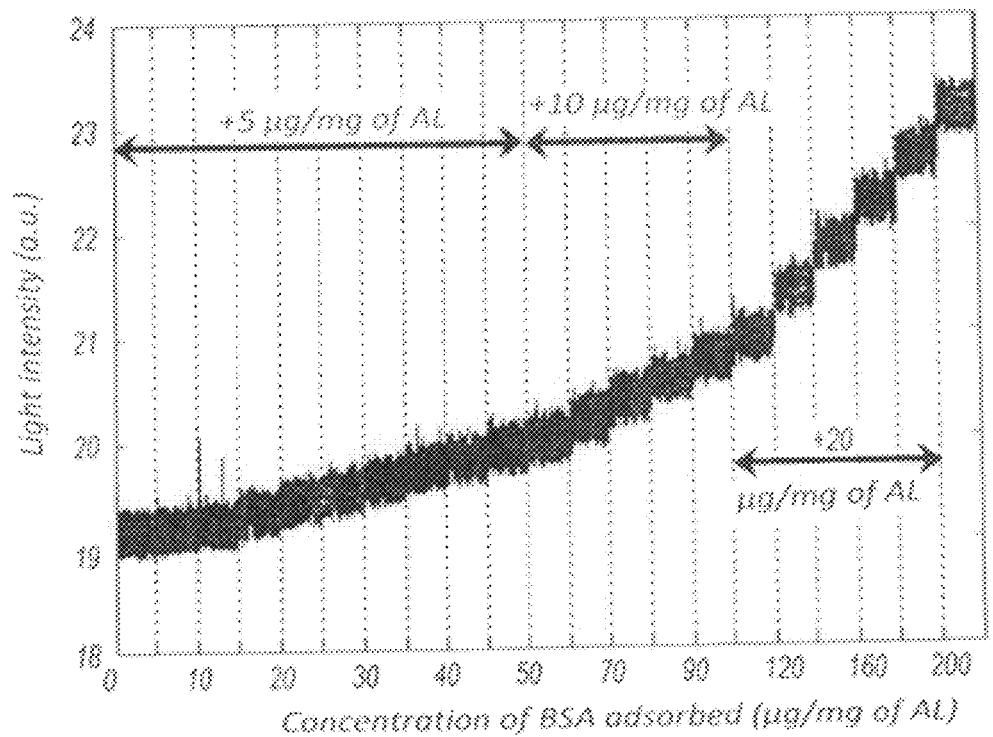
Figure 16:
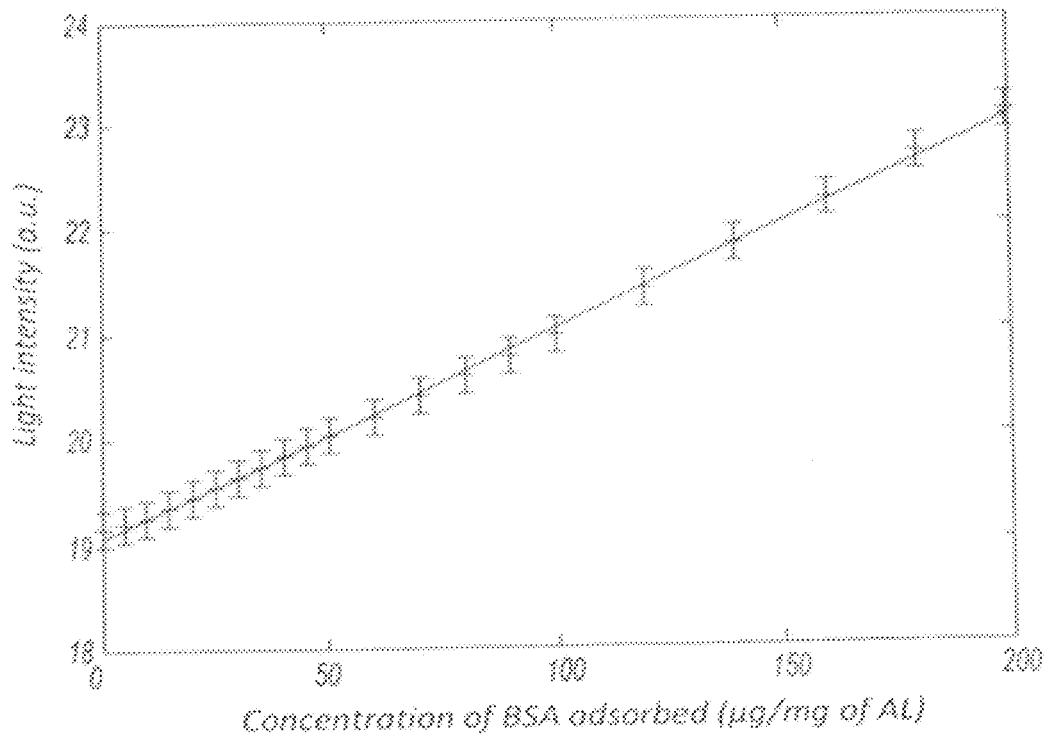
Figure 17:
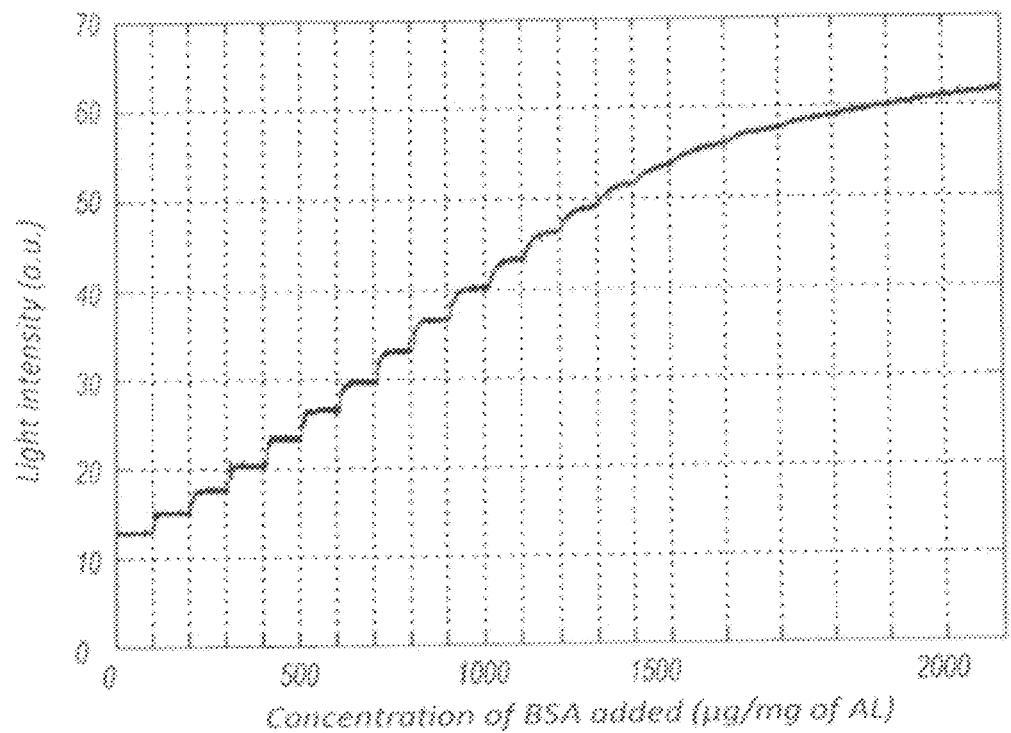
Figure 18:
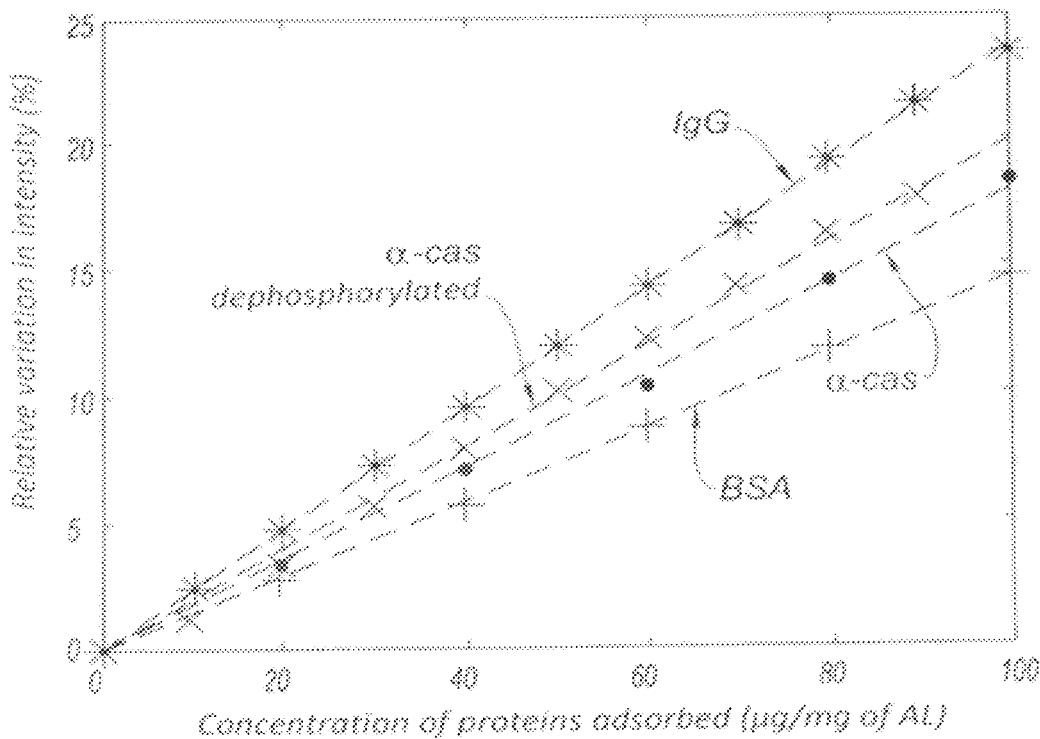
Figure 19:
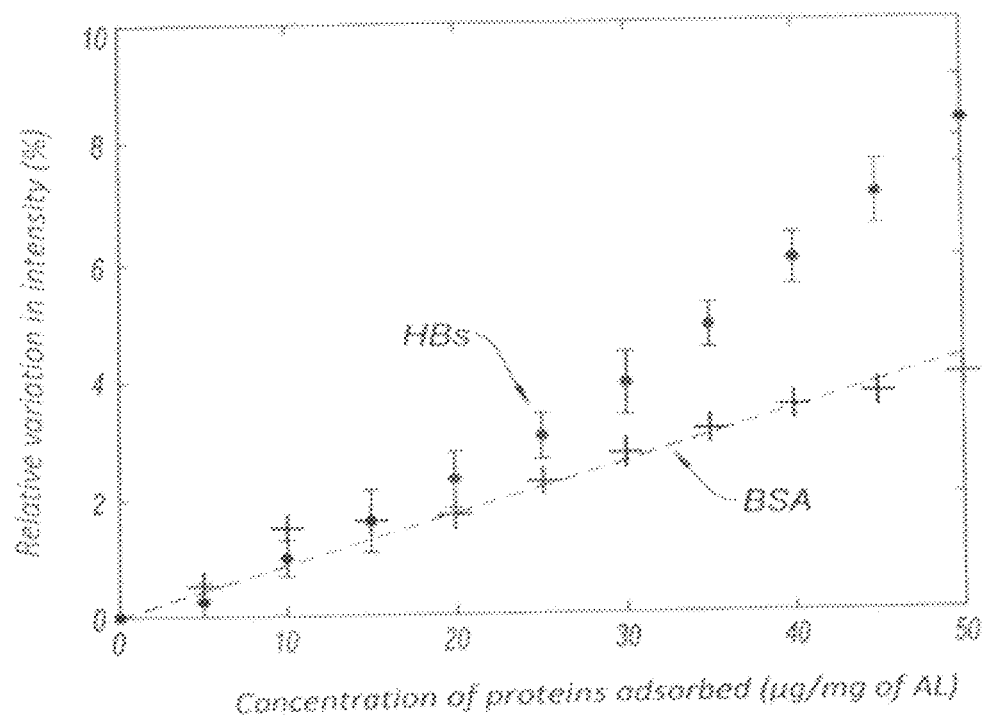
Figure 20:
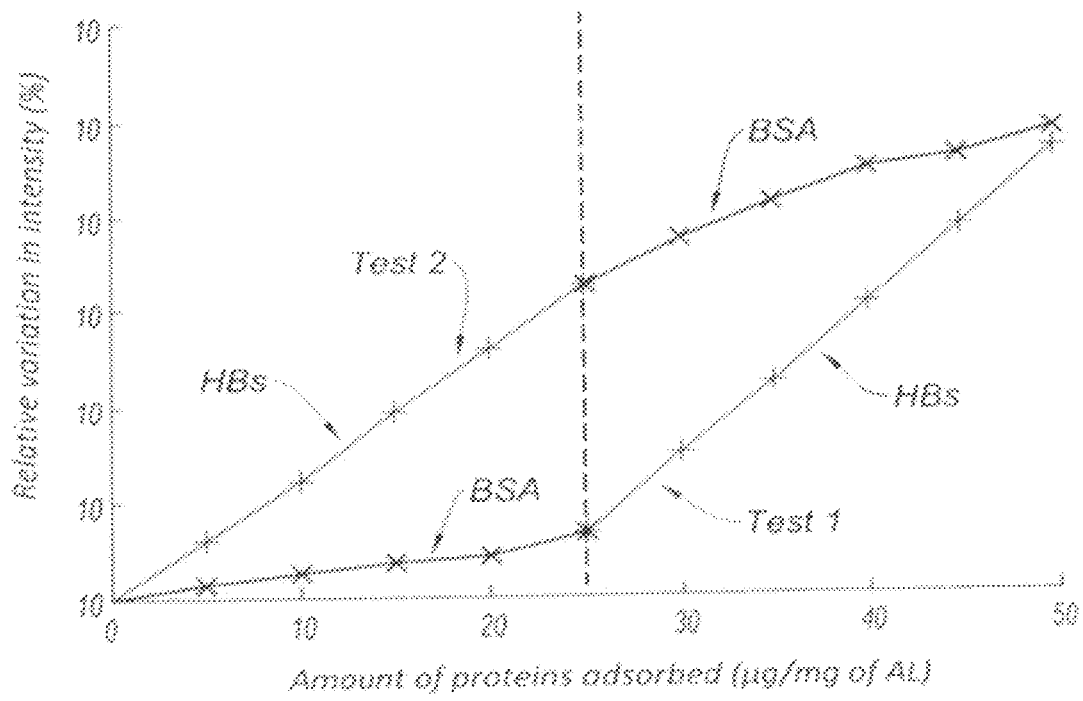
Figure 21:
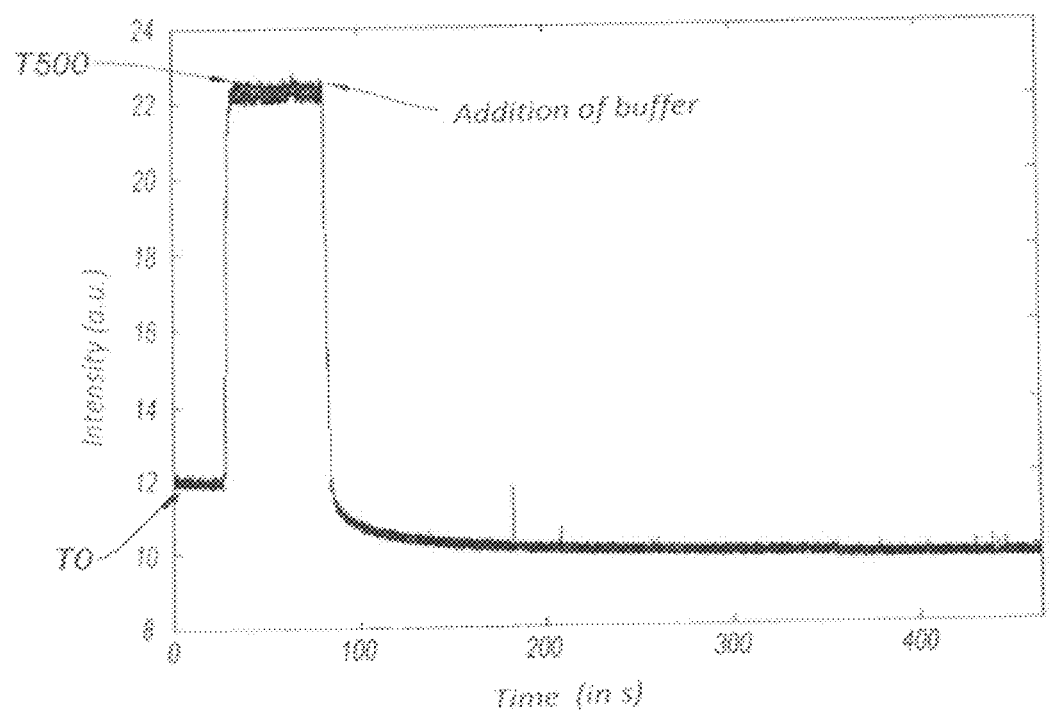

FIG. 5, which comprises FIGS. 5(a) to 5(f), represents images of speckles obtained on the plane of visualization of a device in accordance with that of FIG. 4, in the context of tests carried out with various concentrations of the entity intended to be adsorbed onto the microparticles in suspension in the solution according to the method in accordance with the invention;

FIG. 6, which comprises FIGS. 6(a) to 6(c), represents images of speckles obtained on the plane of visualization of a device in accordance with that of FIG. 4, for various buffer solutions;

FIG. 7 represents the change in the average size of the speckles, according to two directions (Ox and Oy) as a function of the concentration of entity in the solution comprising the microparticles, when said solution is a TRIS (trishydroxymethylaminomethane) buffer solution, in a transmission configuration;

FIG. 8 represents the change in the average size of the speckles, according to two directions (Ox and Oy) as a function of the concentration of entity in the solution comprising the microparticles, when said solution is a phosphate buffer solution, in a transmission configuration;

FIG. 9 represents a detail of FIG. 7, over a reduced concentration range;

FIG. 10 represents the change in the average intensity of the speckle image as a function of the concentration of entity in the solution comprising the microparticles, when said solution is a TRIS (trishydroxymethylaminomethane) buffer solution, in a transmission configuration;

FIG. 11 sets out the principle of the method according to a "backscattering" configuration;

FIG. 12 represents the change in the average size of the speckles, according to one direction, as a function of the concentration of entity in the solution comprising the microparticles, when said solution is a TRIS buffer solution, in a backscattering configuration;

FIG. 13 represents the change in the average intensity of the speckle image as a function of the concentration of entity in the solution comprising the microparticles, when said solution is a TRIS buffer solution, in a backscattering configuration;

FIG. 14 represents a variant of a device that can be used to implement the method according to the invention, operating by backscattering;

FIG. 15 represents the change in the average intensity of the speckle image obtained by adding BSA protein to a TRIS solution comprising the microparticles, as a function of the concentration of proteins adsorbed with the device of FIG. 14;

FIG. 16 is another representation of the results presented in FIG. 15;

FIG. 17 represents the change in the average intensity of the speckle image obtained by adding BSA proteins to a TRIS solution comprising the microparticles, as a function of the concentration of proteins added, with the device of FIG. 14, for a BSA protein concentration range that is extended compared with FIG. 15;

FIG. 18 represents various curves, each of these curves showing the change in the average intensity of the speckle image obtained by adding proteins of predetermined nature to a TRIS solution comprising the microparticles, as a function of the concentration of proteins added, these curves being obtained with the device of FIG. 14;

FIG. 19 is similar to FIG. 18, but for other proteins;

FIG. 20 is similar to FIG. 18, but for the successive addition of two distinct proteins, in the case in point the BSA protein and the hepatitis B antigen;

FIG. 21 represents principally the change in the average light intensity of the speckle image obtained by adding a PHOS buffer solution to a TRIS solution comprising BSA proteins already adsorbed onto microparticles in suspension in the solution, as a function of time;

FIG. 22 represents another device that can be used to implement the method according to the invention, operating by backscattering;

FIG. 23 represents a variant of the device of FIG. 22.

Generally, the invention relates to the monitoring of the depositing of entities on microparticles in suspension in a solution. Preferably, the size of the entities is at least 10 times less than the size of the microparticles.

The method according to the invention makes it possible to estimate the amount of entities deposited on microparticles in suspension in a solution. This method comprises the following steps:
 (a) the solution is illuminated with a light source;
 (b) an optical signal formed by the scattering, in the solution of the illuminating light, is detected, it being possible, for example, for this optical signal to be at least one speckle image;
 (c) the optical signal obtained in step (b) is analyzed in order to obtain an indicator relating to this signal;
 (d) the indicator obtained in step (c) is compared with a reference indicator obtained for a reference solution, the comparison making it possible to estimate the amount of entities deposited on the microparticles.

The term "micrometric particles" or "microparticles" is intended to mean particles having a diameter (or a largest diagonal) of between 0.1 μm and 100 μm, typically 1 μm to 15 μm, for example 3 μm.

The microparticles may be of organic or mineral nature.

In the case of mineral microparticles, they may in particular be mineral salts known as vaccine adjuvants, such as calcium salts, iron salts or, more commonly, aluminum salts. These salts may be hydroxides, in particular oxyhydroxides, phosphates such as hydroxyphosphates or orthophosphates, sulfates, etc., or else mixtures thereof, in particular mixtures of hydroxides and of phosphates.

In the exemplary embodiments of the invention, the microparticles are aluminum microparticles.

These microparticles are contained in a liquid solution, such as an aqueous solution, for example a suitable saline buffer, for example TRIS (trishydroxymethylaminomethane). The concentration of these particles in the solution is generally between a few hundred mg/l and a few tens of g/l, preferably between 1 g/l and 10 g/l. These concentrations make it possible to obtain an image of the speckles owing to light scattering in the solution.

The expression "depositing of an entity on a microparticle" is intended to mean the adsorption of this entity onto the microparticle, but also, more generally, the creation of a bond between an entity at the surface of a microparticle, it being possible for the bond to be, for example, a covalent, electrostatic, ionic, hydrogen, halogen or metallic bond.

The entities which are deposited on the microparticles may be of varied nature.

They may be chemical compounds or biological substances, such as proteins, peptides, polysaccharides, glycoproteins, lipids, glycolipids, polynucleotides, viruses or bacteria.

In the case of the application of the invention to vaccine formulation, these entities may be antigens or compounds exerting an adjuvant activity. The present invention has in particular been implemented with a model protein as entity: bovine serum albumin (BSA). Generally, a BSA protein has a size of between a few nm and a few μm. Generally, the BSA protein has a size of between 1 nm and 200 nm, such that it can be described as a nanometric entity.

The expression quantifying the deposit of entities on the microparticles is intended to mean, for example, estimating an average amount of entities deposited, for example by adsorption, on the microparticles.

The terms "Speckle" or "Speckle grains" are equivalent.

The term "matrix imager" denotes any image sensor which is in a matrix form. By way of example, it may be a CCD (charge coupled device), CMOS (complementary metal oxide semiconductor) or photodiode matrix.

The indicator relating to a speckle image may be an average size, according to a given direction or a given surface, of the speckles of said image.

This indicator may be obtained by calculating the autocorrelation function of the image analyzed.

As a variant, this indicator may also correspond to the average size of the speckles of a plurality of images obtained according to analogous measurement configurations.

According to another variant, the indicator relating to a speckle image may also be the intensity of the speckle image, such an intensity being obtained by constructing the integral of all or part of the pixels of this image. This amounts to adding the value of the pixels contained on all or part of this image.

This indicator may also be the average intensity of a plurality of images of speckles obtained according to analogous measurement configurations.

Irrespective of the nature of the indicator selected, this indicator is generally expressed relative to a reference indicator. For example, it is possible to compare an indicator measured on one image and to compare it with the same indicator, termed initial indicator, established on an initial image. This comparison is then expressed in the form of a relative indicator, for example in the form of a ratio between the measured indicator and the initial indicator, or else in the form of a subtraction of the measured indicator with respect to the initial indicator.

The operating principle of the measuring device will presently be described with reference to FIGS. 1 to 3.

Figure 1:
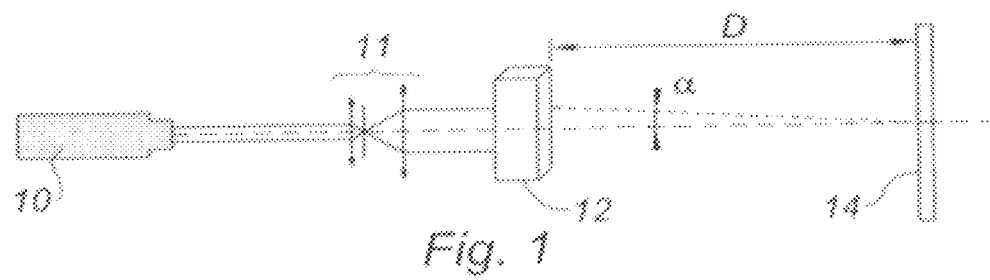

FIG. 1 sets out the principle of implementation of the method according to the invention, according to a first embodiment, termed "transmission".

This consists in illuminating, with a coherent light, for example derived from a laser radiation source 10 and preshaped by dedicated means 11, a solution contained in a container 12 and comprising microparticles in suspension. This is step (a) of the method.

The microparticles in suspension in the solution scatter the incident light originating from the laser 10 and form speckles 13 (also known as speckle grains) at the surface 14 of a matrix imager, also called visualization plane. It is then possible to detect, in the visualization plane 14, an image of speckles 15 formed by the light scattering in the solution. This is step (b) of the method.

Figure 2:
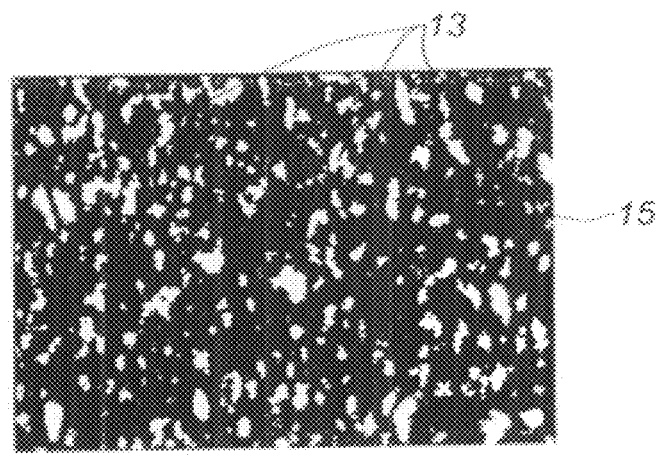
FIG. 2 represents an example of an image obtained according to this configuration.

FIG. 2 represents a speckle image 15 detected by the surface 14 of the matrix imager, this image comprising several speckles 13.

The sizes of these speckles 13 depend on the measurement configuration, namely the type of matrix imager, the distance D between the matrix imager 14 and the container 12 that can be likened to a cuvette, and the orientation α of the matrix imager 14 relative to the cuvette 12, but also on the optical properties of the solution. It is then understood that, when the measurement configuration is fixed, the sizes of the speckles depend only on the optical properties of the solution present in the container.

The speckle image 15 obtained on the surface 14 of the matrix imager cannot, however, be directly exploited.

It is then necessary to have an indicator, relating to this speckle image, that can be correlated with the optical properties of the solution. This is step (c) of the method.

As mentioned above, this indicator may be the average size of the speckles 13 included in the speckle image 15. Such an indicator may be obtained by performing a spatial autocorrelation calculation on the speckle image 15. This autocorrelation calculation is, for example, carried out with the following formula (R1):

$$A(x,y) = FT^{-1}[FT^2(I(x,y))]$$

where: $A(x, y)$ is the image of autocorrelation at the coordinates $(x, y)$ of the visualization plane 14, FT denotes the Fourier transform and $I(x, y)$ is the intensity of the light obtained at the coordinates $(x, y)$ of the visualization plane 14.

This autocorrelation calculation makes it possible to have access to the average dimensions of a speckle according to a given direction, by determining a profile of the autocorrelation image according to said direction, and by calculating the mid-height width of the peak present in this profile. The direction may, for example, be the direction according to an axis Ox (or according to an axis Oy) of the speckle image 15. This aspect will be detailed in the subsequent description.

Figure 3:
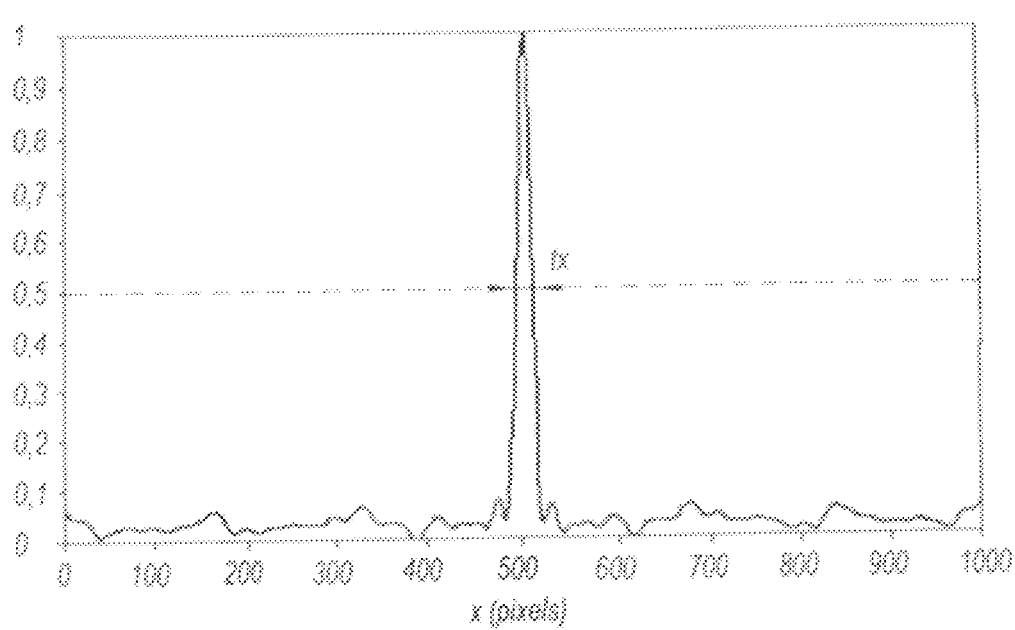
FIG. 3 shows a profile of an autocorrelation image.

FIG. 3 represents a profile, according to a direction Ox, of the standardized autocorrelation image along the y-axis as a function of a number x of pixels along the x-axis and on which the average horizontal size tx of the speckles, expressed in pixels, at mid-height of the peak is specified.

The coherent light used in step (a) to illuminate the solution is monochromatic, and preferably continuous. The wavelength considered is less than the size of the microparticles.

As described above, the indicator may be an average size of the speckles according to a given direction. It may be obtained, for a given image, by calculating the autocorrelation function for this image, for example by means of the formula R1. This makes it possible to obtain an average size of the speckles, or average size of the grains of the speckle image, according to a given direction. This indicator may be determined by constructing a profile of the autocorrelation image, according to said given direction, and by applying a criterion to this profile. The term "profile" is intended to mean a histogram of the intensity of the pixels of the image under consideration according to a given line. The criterion applied to the profile may be the mid-height width of the peak appearing in the profile of the autocorrelation image. This indicator may also be the area of a fraction of the autocorrelation peak constructed according to a given surface.

Of course, other autocorrelation techniques known to those skilled in the art can be used. Generally, any technique which makes it possible to obtain an indicator expressing an average size of the speckles may be used.

The indicator may also be the average, determined on a plurality of images produced under analogous conditions, of average sizes of speckles, obtained on each image.

Step (d) finally makes it possible to estimate the average amount of entities adsorbed onto the microparticles, after having performed a calibration as will be subsequently explained.

Tests which show the feasibility of the method are presented hereinafter.

A diagram of the experimental apparatus used to implement the method is represented in FIG. 4.

The laser radiation source 1 selected is a laser diode emitting a continuous light, having a wavelength of 532 nm and a power of 200 mW.

The light resulting from the laser 1 is guided by a light delivery means 2 such as an optical fiber. This delivery means 2 is optional.

An optical light-shaping means 3 is optionally provided. It may comprise a set of lenses, one or more filters, and in particular a polarizing filter.

The set of lenses is particularly useful if the light source is a laser diode, this being in order to make the beam as fine as possible.

A polarizing filter is particularly useful if the polarization of the light emitted by the laser, or where appropriate the laser diode, is insufficient.

A container 4 intended to receive the solution is inserted into a housing of the device provided for this purpose.

The distance between the laser 1 and the container 4 is approximately 10 cm.

The container 4 used in the tests has dimensions of 1 cm×1 cm×4 cm and its walls are made of glass. Its volume is therefore a few $cm^3$.

More generally, the container may have a depth of between 1 mm and 5 cm, typically between 5 mm and 3 cm. The depth is a dimension taken parallel to the axis of the incident light beam. The depth is defined according to the optical properties of the solution containing the microparticles, and in particular the scattering and absorption properties.

The walls of the container 4 may also be made of an organic or inorganic transparent material, and for example glass or a plexiglass. The important factor is that the walls are transparent to the incident light. These walls may each have a thickness of between 10 μm and a few cm, for example between 10 μm and 3 cm.

A matrix imager 6, in this case a CCD matrix, of 1024×960 pixels, placed downstream of the container 4, forms a plane of visualization of the speckles generated by the light scattering in the solution.

The distance between the container 4 and the CCD matrix is optimized so as to obtain speckles of which the size is about n×n pixels, with n between 2 and 10. This makes it possible, for a given number of pixels of the CCD matrix 6, to obtain a sufficient number of speckles on this CCD matrix while at the same time allowing a sufficiently precise estimation of the sizes of the speckles, and in particular of their average sizes.

In the context of the tests presented here, n=3. The distance between the container 4 and the CCD matrix 6 is then approximately 10 cm.

Moreover, optionally but preferentially, the device comprises a diaphragm 5 between the container 4 and the CCD matrix 6.

This diaphragm 5 makes it possible to eliminate the photons of light that have scattered several times in the solution. This is particularly advantageous when the solution is a highly scattering solution (scattering coefficient greater than a few $cm^{-1}$), in which there are numerous multiple scatterings. The diaphragm 5 makes it possible to improve the contrast of the image of the speckles obtained on the CCD matrix 6. When it is used, the diameter of the diaphragm 5 may be adjusted so as to obtain a contrast of the speckle images on the CCD matrix 6 of greater than 0.9.

In the context of the tests presented here, the diameter of the diaphragm is 5 mm, which makes it possible to obtain the contrast of 0.9 mentioned above.

In addition, optionally but preferentially, a polarizing filter (not represented) may be added between the container 4 and the CCD matrix 6. Its function is to eliminate the multi-scattered photons, photons in fact losing their polarization when they are multi-scattered. This is particularly advantageous when the solution is highly scattering, this being in order to improve the contrast of the speckle images obtained on the CCD matrix 6.

Finally, the CCD matrix 6 is connected to a processing and analyzing means 8, for example a computer, the latter making it possible to carry out the various processings necessary, and in particular the analyses of step (c) of the method.

For these tests, the microparticles in suspension in the solution are aluminum (AlOOH) microparticles, said solution being commonly denoted by the term "gel". These microparticles have an average size of 3 μm. The concentration of the microparticles in the solution is such that the concentration of the aluminum microparticles is 1.5 g/l.

The entity under consideration here is a model protein, in the case in point bovine serum albumin (BSA).

Several solutions have been tested: firstly, a trishydroxymethylaminomethane (TRIS) buffer solution at fixed pH and, secondly, a phosphate buffer solution at fixed pH.

In a first series of tests, the applicant used a TRIS buffer solution at pH=6.8, containing aluminum microparticles in suspension, with the BSA concentration being varied from one test to the other.

The reference solution corresponds to this solution, in the absence of BSA.

For each test carried out, a given amount of BSA is introduced into the solution containing the aluminum microparticles in suspension in the solution.

The amount of BSA introduced into the solution is determined so as to obtain a certain concentration of BSA, hereinafter expressed in μg of BSA per mg of aluminum (denoted by the symbol Al), in the form of aluminum microparticles. Expressing this concentration relative to the amount of aluminum in solution makes it possible to be free of the change in concentration of BSA in the solution itself.

Specifically, the mechanism of adsorption of BSA, and more generally of an entity as defined above, at the surface of the microparticles in suspension can be broken down into three phases.

A first phase during which the BSA proteins mix in the solution (diffusion, convection, etc.) and are transported to the microparticles in suspension.

A second phase during which the BSA proteins are adsorbed at the surface of the aluminum microparticles in suspension.

Finally, a last phase which corresponds to a dynamic equilibrium system. In this system, the amount of BSA adsorbed no longer changes and, consequently, the sizes of the speckles no longer change.

FIG. 5 represents several images of speckles obtained, in a dynamic equilibrium system, at the level of the CCD matrix 6, during step (b). In this FIG. 5, the BSA concentration is represented by Tx where x is the BSA concentration expressed in μg of BSA/mg Al.

FIG. 7 shows the average size, according to two perpendicular directions (Ox and Oy), of the Speckle grains for various concentrations, ranging between T0 and T1000. Each average size is obtained by calculating the autocorrelation function of the corresponding Speckle image, this autocorrelation function taking the form of a peak, and by determining the mid-height width of this peak according to the direction under consideration, in the case in point Ox or Oy, in accordance with what is described above in support of FIG. 3.

It is understood that T0 is a TRIS buffer solution at pH=6.8 containing aluminum microparticles in the form of a gel, but no BSA proteins. It is therefore the reference solution.

The concentrations thus tested range between T0 and T1000. The term Tx denotes a solution in which the amount of BSA proteins added is such that a concentration of x μg of BSA/mg of aluminum is obtained.

It should be noted that these concentration levels are sufficiently low so that, once the equilibrium system is reached, it can be considered that virtually all the proteins added are adsorbed onto the microparticles. The equilibrium system is reached after a period of time ranging from a few seconds to a few hours.

By comparing the various images of FIG. 5, and especially the results presented in FIG. 7, it is observed that, the higher the BSA concentration, the smaller the size of the speckles, or Speckle grains, and naturally vice-versa.

This phenomenon therefore implies that the average size of the speckles is correlated with the amount of proteins adsorbed at the surface of the aluminum microparticles. Thus, when this amount is unknown, measuring the average size of the speckles can make it possible to estimate the average amount of proteins adsorbed onto the microparticles, by means of a comparison with a reference measurement.

This is surprising since those skilled in the art would, on the contrary, have considered that the adsorption of entities of small sizes onto the microparticles would not have modified the sizes of the Speckle grains.

This reference measurement may, for example, be the average size of speckles generated by the "reference" solution of microparticles, before the addition of the BSA proteins. It will be understood that, preferentially, the two measurements (reference measurement and measurement on the solution to be characterized) will be carried out under identical conditions: same device, same concentration of aluminum microparticles, same processing of the signal applied to the Speckle images.

The size of a BSA protein is much smaller than the size of a particle, and those skilled in the art could think that the adsorption of these proteins onto the particles would not be able to be detected, since the size of the microparticle would change only very little before and after the adsorption. However, the experiment proved the opposite, as shown by the results previously commented upon.

The comparison of the average size of the speckles obtained for a given concentration of BSA in the solution in comparison with the reference solution gives information on the amount of BSA proteins adsorbed onto the microparticles.

The inventors carried out another series of tests, replacing the TRIS solution with a phosphate buffer, much less favorable to the adsorption of the BSA proteins onto the aluminum microparticles. This is because, in such a solution, the phosphate ions have a tendency to agglomerate at the surface of the microparticles. Consequently, the adsorption of the proteins at the surface of the microparticles is impeded by the presence of the phosphate ions on the adsorption sites.

During this second series of tests, a phosphate buffer solution at pH=6.8 containing aluminum microparticles in the form of a gel at the same concentration and BSA proteins at a concentration of between T0 and T1000, i.e. between 0 µg of BSA/mg Al and 1000 µg of BSA/mg Al, was used.

FIG. 6 represents, respectively in FIGS. 6(a) to 6(c), the image of the speckles obtained on the CCD matrix 6 during step (b) of the method for the reference solution (FIG. 6a), for the TRIS buffer solution at pH=6.8 (FIG. 6b) at the concentration T1000 and for the phosphate buffer solution at pH=6.8 at the concentration T1000 (FIG. 6c).

FIG. 8 represents, for each concentration, the average sizes of the speckle grains using a phosphate buffer.

It may be noted, in this FIG. 8, that the change in the average size of the speckles as a function of the concentration of the amount of BSA proteins in the solution that are added is less marked than when the TRIS solution is used. As it happens, the adsorption of BSA proteins at the surface of microparticles is much more limited in the case of a phosphate solution than in the case of a TRIS solution for the reasons recalled above.

This comparison then makes it possible to confirm that the change in the size of the Speckle grains is due to the amount of BSA proteins adsorbed at the surface of the aluminum microparticles.

FIG. 9 represents a subset of FIG. 7 (TRIS solution) for low concentrations of BSA proteins added to the solution of microparticles. It is noted that the decrease in the average size of the Speckle grains is detectable starting from low amounts of added proteins, for example T30.

Thus, not only is it possible to estimate the amount of entities adsorbed at the surface of the microparticles by determining an average size of the Speckle grains, but this estimation can be carried out when the amounts of adsorbed entities are low, about a few tens of µg of BSA/mg Al.

Indicators relating to the speckle images other than the indicator concerning the average size of the Speckle grains were tested.

For example, the change in an indicator based on the average intensity of speckle image was also determined. For this, a plurality of speckle images corresponding to a given concentration of entities, in the case in point of BSA proteins, is acquired. The intensity of each of these images is determined by constructing the integral of the image, i.e. by adding the weight of the pixels constituting the image and then calculating the average value of the intensities of each image.

FIG. 10 shows the change in this indicator as a function of the concentration of BSA proteins added to a TRIS solution containing aluminum microparticles. A decrease in this indicator as a function of the increase in the concentration of BSA proteins is again noted.

Thus far, tests carried out with a device operating with a transmission configuration, according to which the container 4 is placed between the laser light source and the matrix imager, have been described.

According to another embodiment, the measurement configuration of the device is a "backscattering" configuration, the light source and the matrix imager then being located facing the same face of the container 4.

Such a measurement configuration is presented in FIG. 11.

In this FIG. 11, a laser radiation source 10 illuminates a part of a container 12, the scattered radiation being collected by a matrix imager 14, the optical axis 141 of which is at an angle $\alpha$ to the optical axis 101 of the laser source 10. This angle $\alpha$ is less than 45°, and preferably between a few degrees and 20°, 12° in the present case. Preferentially, the angle $\alpha$ will be chosen to be as small as possible. Polarizing filters 11, 11' are placed, respectively, between the laser light source 10 and the container 12 (the filter 11 is then called polarizer) and between the container 12 and the matrix imager 14 (the filter 11' is then called analyzer). In particular, a diaphragm may be placed between the container 12 and the imager 14.

Contrary to the transmission embodiment, these filters are oriented orthogonally with respect to one another, so as to eliminate the light reflected by the container, this reflected light being polarized in the same way as the incident light. The laser radiation source 10 and the matrix imager 14 are those previously selected for the tests carried out in transmission mode.

FIG. 12 represents the change in the average size of the speckles then detected by the CCD imager 14, as a function of the concentration of BSA proteins added to a container comprising aluminum microparticles in a TRIS solution. The size is an average size taken according to an axis Ox and expressed in pixels.

A change in the average size of the speckles as a function of the amount of BSA proteins adsorbed onto microparticles is once again observed, such that the average size of the speckles can be considered to be an indicator of this amount.

However, contrary to the case previously described (cf. FIGS. 7 and 9), the function connecting the average size of the speckles to the amount of proteins adsorbed is an increasing function, apart from a few fluctuations.

The change in the average intensity of the speckle images as a function of the amount of BSA proteins adsorbed at the surface of the microparticles was also determined (cf. FIG. 13), the determination of this intensity being carried out in a manner analogous to the first embodiment (FIG. 10), i.e. according to the transmission configuration represented in FIG. 4. For a given concentration of BSA proteins, a plurality of speckle images, typically a few tens (and 50 in this example) is then acquired, it being possible to determine the intensities of said images by determining, for example, the integral of the pixels on all or part of the speckle image detected by the CCD imager. The average intensity of the speckle images obtained is then determined at each concentration of BSA proteins added.

Contrary to the results obtained on the basis of an indicator relating to the size of the speckles, the results of which are presented in FIG. 10, a function which is substantially increasing, except for a few measurement fluctuations, is obtained. The average intensity of the speckle images can therefore be considered to be an indicator of the amount of proteins adsorbed onto microparticles.

Other tests were carried out with a backscattered configuration of the device.

The device is represented in FIG. 14.

In this FIG. 14, a laser radiation source 10' illuminates a part of a container 12', the scattered radiation being collected by a matrix imager 14', the optical axis 141' of which is at an angle $\alpha$ to the optical axis 101' of the laser source 10'. Polarizing filters 11", 11''' are placed, respectively, between the laser light source 10' and the container 12' and between the container 12' and the matrix imager 14'.

The laser radiation source 10' may be a DPSS laser (for "Diode-Pulsed Solid State" laser) emitting a wavelength of 532 nm. The container 12' may be a crystallizing dish with magnetic stirring.

The angle α is less than 45°, and preferably between a few degrees and 20°, in the present case about twenty degrees. Preferentially, the angle α will be chosen to be as small as possible.

The polarizing filter 11" may be a diaphragm, for example of 3 cm in diameter, when the container is a crystallizing dish with magnetic stirring, in order to limit the effects of reflection on the magnetic stirrer of the crystallizing dish.

The polarizing filter 11''' (analyzer) may be a crossed polarizer located between the container 12' and the matrix imager 14', in a manner similar to the device represented in FIG. 11. It makes it possible to improve the quality of the signal reflected by the container 12', in particular when the solution is highly scattering.

Moreover, it should be noted that a diaphragm (not represented) may also be added between the container 12' and the matrix imager 14' in order to eliminate the light photons that have scattered several times in the solution. This is particularly advantageous when the solution is a highly scattering solution (scattering coefficient greater than a few $cm^{-1}$).

The distance between the container 12' and the matrix imager 14' is approximately 20 cm.

The matrix imager 14' is, in the case in point, a FLEA2 camera.

The conditions of test carried out with the device represented in FIG. 14 are the following.

The microparticles in suspension in the buffer solution containing the container 12' are aluminum hydroxide (AlOOH) microparticles. The average size is 3 microns.

The entity considered is always bovine serum albumin (BSA).

The buffer solution is a TRIS solution, of pH=6.8.

In a first test, the results of which are presented in support of FIG. 15, the BSA concentration ranged from 0 to 200 μg of BSA/mg of aluminum. These concentrations are low and are of interest since this is the level of concentration generally encountered in the vaccine formulation field.

The test consisted in successively introducing a certain amount of BSA into the buffer solution comprising the aluminum microparticles.

An amount of 5 μg of BSA/mg of aluminum was added every 100 s, up to 50 μg of BSA/mg of aluminum. An amount of 10 μg of BSA/mg of aluminum was then added every 100 s, up to 100 μg of BSA/mg of aluminum. Finally, an amount of 20 μg of BSA/mg of aluminum was added every 100 s, up to 200 μg of BSA/mg of aluminum.

FIG. 15 represents the light intensity (arbitrary unit) obtained at the level of the matrix imager 14', as a function of the change in the amount of BSA adsorbed/mg of aluminum. It should be noted that the amount of protein added to the buffer solution corresponds to the amount adsorbed by the aluminum microparticles, as long as the solution has not reached saturation.

The light intensity in this case forms the indicator relating to the speckle image captured by the matrix imager 14'. It is obtained by adding together the value of pixels contained on all or part of this image.

It is noted that the increase in the amount of BSA is reflected by an increase in the light intensity obtained on the camera. Moreover, the jump in intensity obtained at each addition of BSA is directly linked to the amount of BSA introduced each time.

This clearly demonstrates the link between the amount of BSA proteins adsorbed onto the aluminum microparticles and the light intensity received by the matrix imager 14'.

FIG. 16 represents the average values, for each stage of introduction of BSA proteins to the buffer solution, of the crude results represented in FIG. 15 (the scale is not linear along the x-axis in FIG. 15, contrary to FIG. 16). It is noted that the intensity increases linearly with the BSA protein concentration.

It should be noted that the authors carried out a similar test without introducing BSA proteins into the TRIS buffer solution, and observed no change in the light intensity comparable to that of FIG. 15. Moreover, the authors also carried out other tests with a PHOS buffer solution, on the one hand, with the addition of BSA proteins and, on the other hand, without the addition of BSA proteins. The PHOS buffer is known to inhibit the adsorption of BSA proteins onto aluminum microparticles. These tests show that the change in the light intensity received by the matrix imager 14' was comparable to that obtained for the test with the TRIS buffer, without the addition of BSA proteins.

In order to verify that the invention could also work for higher concentrations of BSA, the authors carried out another test.

The conditions of this test are the same as the test conditions giving the results represented in FIGS. 15 and 16. However, the method of introducing the BSA proteins into the buffer solution is modified.

Specifically, starting from a TRIS buffer solution containing aluminum microparticles in suspension, additions of 100 μg of BSA proteins were carried out, up to 2000 μg of BSA added/mg of aluminum.

It is noted that the light intensity increases with the increase in concentration of BSA proteins. This demonstrates the fact that the invention can be implemented for concentrations going beyond 200 μg of BSA/mg of aluminum. Consequently, applications other than vaccine formulation can be envisioned.

It is also noted that an effect of saturation of the solution occurs at around 1200 μg of BSA/mg of aluminum. Indeed, above this concentration, the change in the light intensity observed at the level of the matrix imager 14' as a function of the amount of BSA is no longer linear, but curves so as to tend toward a constant value.

Others tests were carried out with the device represented in FIG. 14, using proteins other than the BSA protein.

The buffer solution used is a TRIS, of pH=6.8, comprising aluminum microparticles in suspension (AlOOH).

The proteins used are the following: α-cas, dephosphorylated α-cas, IgG and, finally, the BSA protein for reference.

For each test, the concentration of the protein added to the buffer solution is the same, in the case in point 20 mg/ml, in order to obtain comparable measurements from one protein to the other.

The results are represented in FIG. 18. This FIG. 18 shows the relative variation in the light intensity detected by the matrix imager 14', as a function of the amount of proteins adsorbed. The tests were carried out for protein concentrations ranging up to 100 μg/mg of aluminum.

It is interesting to note that the light intensity increases for all the types of proteins tested. It is therefore possible to envision implementing the invention with numerous different proteins.

Moreover, whatever the protein tested, the change remains substantially linear.

However, it is noted that the slope of these linear changes differs from one protein to the other. When the device is used, it will therefore be advisable to know which protein is employed.

Additional tests were carried out, in order to compare the variation in the light intensity captured by the matrix imager 14' as a function of the concentration of proteins adsorbed, for, on the one hand, the BSA protein and, on the other hand, the hepatitis B antigen (HBs).

For these tests, the solution is a TRIS buffer, of pH=6.8, comprising aluminum microparticles in suspension (AlOOH).

The tests were carried out for concentrations of proteins adsorbed ranging up to 50 μg/mg of aluminum.

The results are presented in FIG. 19.

It is noted in this figure that the invention could also be used with the HBs protein.

In the previous tests, it was demonstrated that the invention can be used for various entities.

It should be noted that the invention can also be employed by using, at the same time, several entities of different natures.

This is because, since the slopes of relative variation of light intensity received by the matrix imager 14' differ from one entity to the other (cf. FIG. 18, for example), it is possible to distinguish between the various entities used.

This is illustrated in support of FIG. 20.

In this FIG. 20, the relative variation in the light intensity received by the matrix imager 14' has been represented as a function of the amount of entities adsorbed by the microparticles in suspension.

The entities under consideration are, in the case in point, the BSA and HBs proteins.

In a first test (test 1), BSA proteins were added to the TRIS buffer solution containing only the aluminum microparticles in suspension, up to an amount of 25 μg of BSA/mg of aluminum. The hepatitis B antigens were then added, up to a total concentration of 50 μg/mg of aluminum.

For this first test, the different slopes linked to the various proteins used are clearly observed.

In a second test (test 2), hepatitis B antigens were added to the TRIS buffer solution containing only the aluminum microparticles in suspension, up to an amount of 25 μg of HBs/mg of aluminum. The BSA proteins were then added, up to a total concentration of 50 μg/mg of aluminum.

Once again, the different slopes linked to the various proteins used are clearly observed.

Moreover, it is noted that the final difference (at 50 μg/mg of aluminum) between the two tests is negligible, which shows that the measuring device is additive.

Finally, an ultimate test was carried out with the device represented in FIG. 14. It demonstrates that the invention can be used for measuring the amount of entities desorbed from the microparticles of adjuvants.

Firstly, a TRIS buffer solution comprising aluminum microparticles in suspension was prepared.

Next, an amount of BSA was added to the solution, such that said amount makes it possible to obtain a concentration of 500 μg of BSA adsorbed/mg of aluminum.

Finally, a volume of 30 ml of phosphate (PHOS) buffer at 500 mmol was added to the solution, in order to desorb the BSA proteins, since the phosphate competes with the BSA.

The results of this test are given in FIG. 21.

In this FIG. 21, the change in the light intensity obtained at the level of the imager 14' has been represented as a function of time.

It is noted that the addition of the phosphate buffer actually causes the light intensity detected by the imager 14' to drop, which characterizes the desorption of the BSA proteins.

The desorption kinetics can finally be analyzed in the same way as the adsorption kinetics.

In order to use the results presented above in an industrial context, all that is then necessary is for a calibration to be carried out with the device under consideration in order to obtain the curves, depending on the case, of FIG. 7, 8, 10, 12, 13 or 15 to 21. In particular, a buffer solution, the nature and the sizes of the microparticles, the concentration of the microparticles in the solution and the nature of entities capable of being deposited on/extracted from the microparticles, are selected.

This calibration is carried out such that various calibration measurements are carried out, the amount of entities adsorbed onto the microparticles being controlled.

Once this calibration curve has been obtained, it is then possible to monitor the change in the adsorption of this entity in this particular solution for any subsequent industrial process.

This can be carried out by monitoring the change in the sizes of the speckles obtained on the matrix imager. Thus, by having an indicator relating to a speckle image, or to a plurality of speckle images, it is possible to determine an amount of entities deposited at the surface of microparticles by comparing this indicator with a reference indicator, it being possible for the latter to be established by carrying out a measurement on the solution of microparticles before addition of the entities, or else on a standard solution. This deposited amount of entities will be deduced from this comparison.

This can also be carried out without involving the obtaining of a speckle image.

Indeed, in all the tests presented above, the device used employs a matrix imager, which makes it possible to have access to the image of the speckles formed by the passing of the light through the solution.

However, the matrix imager can be replaced with a photodiode in all the devices represented in FIGS. 1, 4, 11 and 14.

In this case, the photodiode provides only a level of light intensity, which is sufficient to implement the invention. Indeed, an indicator relating to the image of speckles obtained on a matrix imager can in particular be an average light intensity received by this sensor. It is therefore understood that it is not obligatory to detect the image of speckles formed by the scattering of the incident light in the solution.

Moreover, it should be noted that it is not obligatory to provide a source of coherent light (in the case of the laser), even though this is advantageous. For example, it is possible to envision replacing the laser with a light-emitting diode in order to illuminate the solution.

The method described above makes it possible to determine the amount of entities adsorbed onto the microparticles. Since the duration of each measurement is short, generally less than a few seconds, this measurement is compatible with on-line monitoring of an industrial process, i.e. in real time.

It will be understood that such a method also makes it possible to monitor the kinetics of adsorption of the entities onto the microparticles, these kinetics being obtained by comparison of the results from successive measurements.

The method implemented in the context of the invention can also function for a turbid solution of microparticles in suspension. This is particularly advantageous since turbid solutions are in particular encountered in vaccine formulation.

The devices represented in FIGS. 4 and 11 are devices which operate, respectively, by transmission, or by reflection.

Other types of devices can be envisioned.

Thus, the device represented in FIG. 22 is a device which operates by backscattering, which can also be the subject of embodiment variants. It comprises the same means as those present in the device described in support of FIG. 4, these means bearing the same references.

It should, however, be noted that, with the exception of the laser 1 and of the computer 8, the means of this device are integrated in a sealed receptacle 100 which can be immersed in the solution. This receptacle may be likened to a probe that can be immersed in the solution of microparticles in suspension, and the floatability of which is controlled. The cuvette containing the solution is then accessible by means of a window 41, which can be made of glass or of a transparent plastic.

One embodiment variant of this device, which also operates by backscattering, is represented in FIG. 23. The means similar to those presented in the device described in support of FIG. 4 bear the same references. Once again, this device may be sealed and immersible in the solution of microparticles in suspension.

According to this variant, the device is in the form of a receptacle 100 that can be likened to a probe. This probe generally has a diameter of less than 15 cm, preferably between a few centimeters and 10 cm.

This probe 100 is sealed and completely immersible in the solution. To this effect, the laser is replaced with a miniaturized laser diode 1 powered by a battery 9. The processing means 8 is also miniaturized and integrated with the probe 100. In order to communicate with the exterior, a dedicated means 91, capable of transmitting data by radiofrequency or by a wired connection, is envisioned.

The devices presented in support of FIGS. 22 and 23 can, without implied distinction, use a source of light which is coherent (in the case of the laser) or not (in the case of the light-emitting diode). Moreover, the matrix imager can be replaced with a photodiode, providing only a measurement of the light intensity.

What is claimed is:

1. A method for estimating an amount of entities bonded to microparticles in suspension in a solution, which comprises the following steps:
   (a) illuminating a plurality of the microparticles at a time in the solution with a light source;
   (b) detecting an optical signal formed by the scattering of the illuminating light in the solution;
   (c) analyzing the optical signal obtained in step (b) in order to obtain an indicator relating to this signal;
   (d) estimating the amount of entities bonded to the microparticles by comparing the indicator obtained in step (c) with a reference indicator obtained for a reference solution,
   wherein a size of at least one of the entities is at least ten times less than a size of at least one of the microparticles, and
   wherein estimating the amount of entities bonded to the microparticles includes:
      estimating an average amount of entities bonded to the microparticles in the entire solution by comparing the indicator obtained in step (c) with the reference indicator obtained for the reference solution once.

2. The method as claimed in claim 1, wherein the indicator obtained in step (c) corresponds to a light intensity of the optical signal.

3. The method as claimed in claim 1, wherein the optical signal detected in step (b) is at least one speckle image.

4. The method as claimed in claim 3, wherein the indicator obtained in step (c) corresponds to an average size of speckles of said at least one speckle image.

5. The method as claimed in claim 3, wherein the indicator obtained in step (c) corresponds to an average intensity of said at least one speckle image.

6. The method as claimed in claim 1, 2, 3, 4, or 5, wherein the entities have a size of between 1 nm and 10 µm and the microparticles have a size of between 0.1 µm and 100 µm.

7. The method as claimed in claim 1, wherein the microparticles are aluminum microparticles.

8. The method according to claim 7, wherein the entities are antigens.

9. The method as claimed in claim 1, wherein the solution is chosen from one of the following solutions: aqueous solution, a saline aqueous solution, or trishydroxy-methylaminomethane solution.

10. The method as claimed in claim 1, wherein the solution forms a turbid solution of the microparticles in suspension.

11. The method as claimed in claim 1, wherein step (a) is carried out with a coherent light.

12. The method as claimed in claim 1, wherein step (a) is carried out with a monochromatic light.

13. The method as claimed in claim 1, wherein the reference solution involved in step (d) is a solution identical to the solution illuminated in step (a), with the exception of the presence of the entities.

14. The method as claimed in claim 1, wherein the entities are antigen entities.

15. The method as claimed in claim 1, wherein the amount of entities bonded to the microparticles includes an amount of entities adsorbed by the microparticles.

16. The method as claimed in claim 1, wherein the entities bonded to the microparticles are bonded by one of a covalent, electrostatic, ionic, hydrogen, halogen, or metallic bond.

17. The method according to claim 1, further comprising introducing a given amount of the entities to the solution.

18. A device for estimating an amount of entities bonded to microparticles in suspension in a solution, which comprises:
   a light source configured to illuminate a plurality of the microparticles at a time in the solution with light;
   an imager configured to detect an optical signal formed by the scattering of the light in the solution; and
   a processor configured to obtain an indicator based upon the optical signal and to estimate the amount of entities bonded to the microparticles by comparing the indicator with a reference indicator obtained for a reference solution,
   wherein a size of at least one of the entities is at least ten times less than a size of at least one of the microparticles, and
   wherein the processor is further configured to:
   estimate an average amount of entities bonded to the microparticles in the entire solution by comparing the indicator obtained based upon the optical signal with the reference indicator obtained for the reference solution once.

19. The device as claimed in claim 18, wherein the light source and the imager are integrated in a sealed receptacle immersed in the solution.

20. The device as claimed in claim 19, wherein the processor is integrated in said sealed receptacle.

21. The device as claimed in claim 18 or 19, further comprising a container containing the solution.

22. The device as claimed in claim 21, wherein the light source and the imager are placed on either side of the container.

23. The device as claimed in claim 18, further comprising light blocker, placed before the imager, that eliminates the light photons that have scattered several times in the solution.

24. The device as claimed in claim 23, wherein the light blocker is a diaphragm.

25. The device as claimed in claim 18, wherein the light source is a source of coherent light formed by a laser.

26. The device as claimed in claim 18, wherein the imager is a matrix imager of CCD, or CMOS, or photodiode type.

27. The device as claimed in claim 26, wherein the matrix imager detects a speckle image as an optical signal.

28. The device as claimed in claim 18, wherein the imager is formed by a photodiode.

29. The device as claimed in claim 18, wherein the processor is configured to estimate an amount of entities adsorbed and/or desorbed on the microparticles in suspension in the solution.

30. The device as claimed in claim 29, wherein the microparticles are aluminum microparticles and the entities are antigen entities.

31. The device as claimed in claim 18, wherein the solution has a given amount of the entities introduced therein.

\* \* \* \* \*